United States Patent
Takahashi (10) Patent No.: US 11,938,255 B2
(45) Date of Patent: Mar. 26, 2024

(54) PERITONEAL DIALYSATE, PERITONEAL DIALYSATE SET, COMPOSITION USED FOR PERITONEAL DIALYSIS, AND METHOD FOR PERITONEAL DIALYSIS

(71) Applicant: TERUMO KABUSHIKI KAISHA, Tokyo (JP)

(72) Inventor: Hiroaki Takahashi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 775 days.

(21) Appl. No.: 16/971,879

(22) PCT Filed: Feb. 27, 2019

(86) PCT No.: PCT/JP2019/007666
§ 371 (c)(1),
(2) Date: Aug. 21, 2020

(87) PCT Pub. No.: WO2019/168063
PCT Pub. Date: Sep. 6, 2019

(65) Prior Publication Data
US 2021/0100942 A1    Apr. 8, 2021

(30) Foreign Application Priority Data
Mar. 1, 2018   (JP) .................. 2018-036394

(51) Int. Cl.
*A61M 1/28* (2006.01)
*A61K 9/08* (2006.01)
(Continued)

(52) U.S. Cl.
CPC ............... *A61M 1/287* (2013.01); *A61K 9/08* (2013.01); *A61K 31/7004* (2013.01);
(Continued)

(58) Field of Classification Search
CPC ... A61M 1/287; A61K 31/7004; A61K 33/14; A61K 9/0019; A61K 9/08; A61K 47/02; A61K 47/26; A61P 7/08
See application file for complete search history.

(56) References Cited

U.S. PATENT DOCUMENTS

| 5,589,197 A | 12/1996 | Shockley et al. |
| 5,629,025 A | 5/1997 | Shockley et al. |

(Continued)

FOREIGN PATENT DOCUMENTS

| EP | 3 671 753 A1 | 6/2020 |
| JP | 2002253667 A | 9/2002 |

(Continued)

OTHER PUBLICATIONS

Japanese Patent Application No. 2002-253667 A (2002).*

(Continued)

*Primary Examiner* — John Kim
(74) *Attorney, Agent, or Firm* — BUCHANAN INGERSOLL & ROONEY PC (57) ABSTRACT

The present invention is to provide a means capable of properly balancing water and sodium in peritoneal dialysis treatment, without causing hyponatremia, while avoiding adversely affecting residual renal function. A peritoneal dialysate containing 1.5 to 1.8 w/v % of glucose and 120 to 130 mEq/L of sodium, and being for independent use once or twice a day, wherein the peritoneal dialysate is used in combination with another peritoneal dialysate that contains 1.35 to 2.5 w/v % of glucose and 132 to 135 mEq/L of sodium, in peritoneal dialysis that involves injection of an amount of 1.5 to 2.0 L per one time in an abdominal cavity of a subject, storage and drainage three to five times a day.

8 Claims, 5 Drawing Sheets

(51) Int. Cl.
   *A61K 31/70*    (2006.01)
   *A61K 31/7004*  (2006.01)
   *A61K 33/14*    (2006.01)
   *A61K 47/02*    (2006.01)
   *A61K 47/26*    (2006.01)
   *A61K 9/00*     (2006.01)
   *A61P 7/08*     (2006.01)

(52) U.S. Cl.
   CPC .............. *A61K 33/14* (2013.01); *A61K 47/02* (2013.01); *A61K 47/26* (2013.01); *A61K 9/0019* (2013.01); *A61P 7/08* (2018.01)

(56) References Cited

U.S. PATENT DOCUMENTS 5,631,025 A     5/1997   Shockley et al.
2006/0079464 A1 4/2006   Sanaka et al.

FOREIGN PATENT DOCUMENTS

JP   2005-531630 A   10/2005
JP       4625657 B2   2/2011

OTHER PUBLICATIONS

Office Action (Notice of Amendment) dated Dec. 15, 2022, by the Patent Office, Department of Intellectual Property in corresponding Thailand Patent Application No. 2001004811 and an English translation of the Office Action. (10 pages).

Office Action (Notice of Reasons for Refusal) dated Nov. 29, 2022, by the Japan Patent Office in corresponding Japanese Patent Application No. 2020-503593 and an English Translation of the Office Action. (8 pages).

The extended European Search Report dated Mar. 1, 2021, by the European Patent Office in corresponding European Patent Application No. 19761432.4-1113. (10 pages).

Office Action (Notice of Opinion for the First Review) dated Dec. 28, 2022, by the People's Republic of China National Bureau of Knowledge and Property in corresponding Chinese Patent Application No. 201980016328.3 and an English translation of the Office Action. (13 pages).

Office Action (The result of Stage I Substantive Examination) dated Mar. 2, 2023, by the Ministry of Law and Human Right of the Republic of Indonesia Directorate General of Intellectual Property in corresponding Indonesian Patent Application No. P00202006626 and an English translation of the Office Action. (4 pages).

Office Action dated Apr. 6, 2023, by the Vietnam Intellectual Property Office in corresponding Vietnamese Patent Application No. 1-2020-04975 and an English translation of the Office Action. (6 pages).

Office Action (Examination Report) dated Jul. 8, 2022, by the Patent Office, Government of India, in corresponding India Patent Application No. 202017036721 with an English Translation of the Office Action. (6 pages).

International Search Report (PCT/ISA/210) and translation and Written Opinion (PCT/ISA/237) dated May 14, 2019, by the Japanese Patent Office as the International Searching Authority for International Application No. PCT/JP2019/007666.

Masaaki, N. et al., "Evidence of peritoneal dialysis fluid, sodium concentration (Na)", Kidney and Dialysis, Jan. 2017, vol. 82, No. 1, pp. 75-79.

Nakayama, M. et al., "Anti-hypertensive effect of low Na concentration (120 mEq/l) solution for CAPO patients", Clinical Nephrology, 1994 (month unknown), vol. 41, No. 6, pp. 357-363.

Nakayama, M. et al., "Low Na concentration solution for CAPD", Clinical Nephrology, 1996 (month unknown), vol. 45, No. 1, pp. 66-68.

Nakayama, M. et al., "Novel Low Na Peritoneal Dialysis Solutions Designed To Optimize Na Gap of Effluent: Kinetics Of Na And Water Removal", Peritoneal Dialysis International, Sep. 2009, vol. 29, No. 5, pp. 528-535.

Nakayama, M. et al., "Study on na concentration of peritonaal dialysis fluid for continuous amblatory periperitoneal dialysis (CAPD)", the Japanese Journal of Nephrology, 1992 (month unknown), vol. XXXIV, No. 8, pp. 913-920.

Takeda, S. "Body HA-3, Drugs In Japan ethical drugs", JIHO, Inc., 2004 (month unknown), pp. 1808-1813.

Office Action (Notice of Second Office Action) dated Jun. 16, 2023, by the State Intellectual Property Office of People's Republic of China in corresponding Chinese Patent Application No. 201980016328.3 and an English Translation of the Office Action. (14 pages).

Office Action (Notice of Reasons for Refusal) dated Nov. 6, 2023, by the Japanese Patent Office in corresponding Japanese Patent Application No. 2023-006354 and an English translation of the Office Action. (8 pages).

Office Action (Hearing Notice) dated Nov. 16, 2023, by the Indian Patent Office in corresponding Indian Patent Application No. 202017036721. (3 pages).

Office Action (Notice of third review opinion) dated Dec. 29, 2023, in corresponding Chinese Patent Application No. 201980016328.3 and English translation of the Office Action. (14 pages).

\* cited by examiner

PERITONEAL DIALYSATE, PERITONEAL DIALYSATE SET, COMPOSITION USED FOR PERITONEAL DIALYSIS, AND METHOD FOR PERITONEAL DIALYSIS

TECHNICAL FIELD

The present invention relates to a peritoneal dialysate, a peritoneal dialysate set, a composition used for peritoneal dialysis, and a method for peritoneal dialysis.

BACKGROUND ART

Peritoneal dialysis is a dialysis method using a peritoneum as a dialysis membrane, and is a method for correcting body fluid disorder, by which metabolites are transferred from blood through the peritoneum into a peritoneal dialysate in an abdominal cavity while being driven by concentration difference (diffusion), meanwhile an excessive body fluid is transferred or removed while being driven by osmotic pressure difference (ultrafiltration or water removal). At present, CAPD (Continuous Ambulatory Peritoneal Dialysis) therapy prevails. In the CAPD therapy, the peritoneal dialysate is injected through a catheter into the abdominal cavity, allowed to store for a predetermined length of time, and then drained, repeating this cycle three to five times a day.

In existing peritoneal dialysate, sodium concentration has been set constant irrespective of glucose concentration, wherein the glucose concentration ranges from 1.35 to 4.00 w/v %, meanwhile the sodium concentration is set to 132 to 135 mEq/L. Such existing peritoneal dialysate can attain an increased water removal as the glucose concentration increases, whereas the amount of sodium removal tends to run short. With sodium remained within the body, a subject will feel thirsty and will drink much water, so that dialytic removal of water would unfortunately result in insufficient ultrafiltration as a consequence, and would even induce plethora if this situation is repeated.

Hence, there has been proposed peritoneal dialysates (Low Sodium Peritoneal Dialysis Solution) having sodium concentration set lower than in serum (Patent Literatures 1 to 3). According to Patent Literatures 1 to 3, an osmoregulator such as amino acid, polypeptide, polyglucose or the like is added to enhance the ultrafiltration performance, to thereby increase the amount of sodium removal from the circulatory system into the peritoneum.

It has also been reported that use of low sodium peritoneal dialysates enables sodium transfer (diffusion) driven by sodium concentration difference, without increasing osmotic pressure (Non-Patent Literatures 1 to 2). According to Non-Patent Literatures 1 to 2, relations between ultrafiltration and sodium removal effect are examined, with the sodium concentration ranged from 100 to 132 mEq/L, while leaving the glucose concentration constant at 1.36 w/v % or 2.27 w/v %.

According to Non-patent Literatures 1 to 2, when sodium concentration in the peritoneal dialysate is reduced at a glucose concentration of 2.27 w/v %, the water removal declines, so that also the amount of sodium removal consequently declines. Ratio of the amount of sodium removal to the ultrafiltration volume however increases, so that the net amount of sodium removal will increase. It has been reported that since the serum sodium concentration does not distinctively change during dialysis, when the peritoneal dialysate with the sodium concentration controlled within the aforementioned range is used, so that the low sodium peritoneal dialysate is reportedly suitable for a patient of sodium overload, preferably with a glucose concentration of 2.27 w/v % and a sodium concentration of 120 mEq/L. Note that Non-Patent Literatures 1 to 2 describe that a glucose concentration of 1.36 w/v % is improper since the water removal will be too small.

As described above, reduction of the sodium concentration in the peritoneal dialysate is typically expected to increase the amount of sodium removal driven by diffusion, but would lower the osmotic pressure due to a decrease of sodium concentration, and would result in lowered water removal. The lowered water removal means insufficient volume of dialysis, and would pose a problem in the treatment. Such improper amount of sodium removal, relative to the water removal, would also cause plethora due to insufficient sodium removal, or would inversely cause hyponatremia due to excessive sodium removal. Patent Literature 4 therefore proposes a peritoneal dialysate capable of removing sodium while being well balanced against the water removal without degrading the ultrafiltration performance, particularly capable of preventing sodium residence.

Non-Patent Literature 3 describes that sodium gap (sodium residence) becomes approximately zero, after 4-hour storage of 2.0 L of each peritoneal dialysate with glucose and sodium concentrations combined as 0.9 w/v % and 133 mEq/L, 1.6 w/v % and 126 mEq/L, or 2.5 w/v % and 118 mEq/L respectively. It has however been described that one-day combined administration of these peritoneal dialysates yields a negative value of daily sodium gap, which ranges from −32 to −48 mEq. The peritoneal dialysate, thus designed to cause no sodium residence, was found to demonstrate a desired effect if the storage time per administration is limited to 4 hours. The storage time in actual clinical use, however, widely varies from 2 to 11 hours. The Non-Patent Literature 3 neither clarifies possible risks of hyponatremia due to excessive sodium removal over one-day administration or continuous administration, nor influences on residual renal function, and also does not disclose any solution to these problems at all.

CITATION LIST

Patent Literatures

Patent Literature 1: U.S. Pat. No. 5,589,197
Patent Literature 2: U.S. Pat. No. 5,629,025
Patent Literature 3: U.S. Pat. No. 5,631,025
Patent Literature 4: JP 2002-253667A

Non-Patent Literatures

Non-patent Literature 1: M. Nakayama, et al., *Clinical Nephrology*, 1994, Vol. 41, No. 6, p. 357-363
Non-patent Literature 2: M. Nakayama, et al., *Clinical Nephrology*, 1996, Vol. 45, No. 1, p. 66-68
Non-patent Literature 3: M. Nakayama, et al., *Peritoneal Dialysis International*, 2009, Vol. 29, No. 5, p. 528-535

SUMMARY OF INVENTION

It is therefore an object of the present invention to provide a means that enables, in peritoneal dialysis treatment, proper management of balance between water and sodium, without causing hyponatremia, and while avoiding any adverse effect exerted on the residual renal function.

The present inventor has conducted extensive examinations to solve the aforementioned problem. As a result, according to a first embodiment of the present invention, provided is a peritoneal dialysate including 1.5 to 1.8 w/v % of glucose and 120 to 130 mEq/L of sodium, and being for independent use once or twice a day, wherein the peritoneal dialysate is used in combination with another peritoneal dialysate that contains 1.35 to 2.5 w/v % of glucose and 132 to 135 mEq/L of sodium, in peritoneal dialysis that involves injection of an amount of 1.5 to 2.0 L per one time in an abdominal cavity of a subject, storage and drainage three to five times a day.

According to a second embodiment of the present invention, provided is a peritoneal dialysate set including a first peritoneal dialysate that contains 1.5 to 1.8 w/v % of glucose and 120 to 130 mEq/L of sodium; and a second peritoneal dialysate that contains 1.35 to 2.5 w/v % of glucose and 132 to 135 mEq/L of sodium, wherein the first peritoneal dialysate and the second peritoneal dialysate are independently used three to five times in total a day in peritoneal dialysis that involves injection of an amount of 1.5 to 2.0 L in an abdominal cavity of a subject, storage and drainage, in which the first peritoneal dialysate is used once or twice a day.

According to a third embodiment of the present invention, provided is a composition for use in peritoneal dialysis, wherein the composition includes 1.5 to 1.8 w/v % of glucose and 120 to 130 mEq/L of sodium, wherein the composition is used in combination with another composition containing 1.35 to 2.5 w/v % of glucose and 132 to 135 mEq/L of sodium for use in peritoneal dialysis, wherein the composition and the another composition are independently injected in an amount of 1.5 to 2.0 L in an abdominal cavity of a subject, stored and drained three to five times in total a day, in which the composition is used once or twice a day.

According to a fourth embodiment of the present invention, provided is a method for peritoneal dialysis including: injecting independently each a first peritoneal dialysate and a second peritoneal dialysate in an amount of 1.5 to 2.0 L in an abdominal cavity of a subject, storing and draining three to five times in total a day, wherein the first peritoneal dialysate contains 1.5 to 1.8 w/v % of glucose and 120 to 130 mEq/L of sodium, and is used once or twice a day, and the second peritoneal dialysate contains 1.35 to 2.5 w/v % of glucose and 132 to 135 mEq/L of sodium.

DESCRIPTION OF EMBODIMENTS

Embodiments according to one aspect of the present invention will be explained below. The present invention is not limited to the embodiments below.

Herein, any range given in the form of "x to y" means "x or more and y or less". All operations and measurements of physical properties are carried out at room temperature (1 to 30° C.)/relative humidity of 40 to 50% RH, unless otherwise specifically noted.

First Embodiment: Peritoneal Dialysate

A first embodiment of the present invention relates to a peritoneal dialysate containing 1.5 to 1.8 w/v % of glucose and 120 to 130 mEq/L of sodium, and being for independent use once or twice a day, wherein the peritoneal dialysate is used in combination with another peritoneal dialysate that contains 1.35 to 2.5 w/v % of glucose and 132 to 135 mEq/L of sodium, in peritoneal dialysis that involves injection of an amount of 1.5 to 2.0 L per one time in an abdominal cavity of a subject, storage and drainage three to five times a day. With such constituent, it now becomes possible, in peritoneal dialysis treatment, to properly manage balance between water and sodium, without causing hyponatremia and while avoiding any adverse effect exerted on the residual renal function.

The peritoneal dialysate according to the first embodiment of the present invention (in this patent specification, also referred to as "first peritoneal dialysate") contains 1.5 to 1.8 w/v % of glucose and 120 to 130 mEq/L of sodium. The first peritoneal dialysate preferably contains 123 to 128 mEq/L of sodium, and more preferably contains 125 to 128 mEq/L of sodium.

The first peritoneal dialysate may further contain any ingredient contained in ordinary peritoneal dialysate. This sort of ingredient is exemplified by calcium, magnesium, chlorine, and alkalizing agent. The first peritoneal dialysate preferably contains 2.0 to 4.0 mEq/L of calcium; 0.5 to 1.5 mEq/L of magnesium; 86.0 to 98.0 mEq/L of chlorine; and 35 to 40 mEq/L of alkalizing agent.

The alkalizing agent is exemplified by lactate ion and bicarbonate ion. Concentration of the alkalizing agent is given by a total of employed lactate ion, bicarbonate ion and so forth, and may typically be 35 to 40 mEq/L of alkalizing agent on the basis of combination of lactate ion and bicarbonate ion. The alkalizing agent is preferably lactate ion.

The first peritoneal dialysate is used in combination with another peritoneal dialysate that contains 1.35 to 2.5 w/v % of glucose and 132 to 135 mEq/L of sodium (in this patent specification, also referred to as "second peritoneal dialysate").

The second peritoneal dialysate may further contain any ingredient contained in ordinary peritoneal dialysate. This sort of ingredient is exemplified by calcium, magnesium, chlorine, and alkalizing agent. The second peritoneal dialysate preferably contains 2.3 to 4.0 mEq/L of calcium; 0.5 to 1.5 mEq/L of magnesium; 95.0 to 105.5 mEq/L of chlorine; and 35 to 40 mEq/L of alkalizing agent.

The alkalizing agent contained in the second peritoneal dialysate may be same as the aforementioned alkalizing agent contained in the first peritoneal dialysate.

The first peritoneal dialysate and the second peritoneal dialysate may further contain other optional ingredients, without damaging the objective of the present invention. For example, the first peritoneal dialysate and the second peritoneal dialysate may contain an organic acid or the like, corresponding to concentration difference between the total cation and chlorine ion, so as to keep electrical neutrality of the peritoneal dialysate. Such organic acid is exemplified by propionic acid, malic acid, fumaric acid, succinic acid, oxalacetic acid, N-acetylglycin, N-acetyl-L-cysteine, glutaric acid, glucuronic acid, ascorbic acid, citric acid, isocitric acid, gluconic acid, N-acetyl-L-aspartic acid, N-acetyl-L-glutamic acid, N-acetyl-L-methionine, N-acetyl-L-proline, N-acetyl-L-valine, N-acetyl-L-glutamine, N-acetyl-L-arginine, N-acetyl-L-histidine, N-acetyl-L-leucine, N-acetyl-L-tryptophan, and salts of them.

pH of the first peritoneal dialysate and the second peritoneal dialysate is usually around pH 5.0 to 7.5, and preferably around pH 6.5 to 7.5.

Osmotic pressure of the first peritoneal dialysate and the second peritoneal dialysate is usually around 300 to 500 mOsm/kg, and preferably around 330 to 450 mOsm/kg.

In peritoneal dialysis, typically an amount of 1.5 to 2.0 L of a peritoneal dialysate is injected in the peritoneum of a subject, allowed to store for 4 to 8 hours, and then drained and removed after expecting the effect. These operations make up one cycle, and three to five times continuous operation per one day are continuously conducted. The first peritoneal dialysate is used in combination with the second peritoneal dialysate. More specifically, the first peritoneal dialysate and the second peritoneal dialysate are independently used three to five times in total a day, in peritoneal dialysis. From among the three to five times in total of the operation, the first peritoneal dialysate is independently used once or twice a day. With such properly combined use of the first peritoneal dialysate and the second peritoneal dialysate, it now becomes possible, in peritoneal dialysis treatment, to properly manage balance between water and sodium, without causing hyponatremia, and while avoiding any adverse effect exerted on the residual renal function.

The subject of the peritoneal dialysis is typically mammal, and preferably human.

An injection volume, storage time and number of times of operation are properly controlled depending on symptom, blood biochemical values and imbalance of body fluid, age, body weight and so forth. An injection rate and drainage rate are usually 300 mL/min or below.

Methods for preparing the first peritoneal dialysate and the second peritoneal dialysate employable here are not specifically limited, and may be any of widely known methods for preparing peritoneal dialysate. For example, employable is a method by which glucose; cation and/or chlorine ion sources such as sodium chloride, calcium chloride, magnesium chloride, sodium lactate, calcium salt, magnesium salt and sodium bicarbonate; acid ingredient and so forth are dissolved in water (water for injection, for example), while controlling the glucose concentration and sodium concentration, as well as optionally controlling concentrations of calcium, magnesium, chlorine, alkalizing agent and so forth, within the aforementioned concentration ranges.

The thus prepared peritoneal dialysate is preferably enclosed in a soft plastic bag or a glass container, and then subjected to high pressure steam sterilization or hot water sterilization. Materials for the soft plastic are exemplified by polyvinyl chloride, polypropylene, polyethylene, polyester, polyamide, ethylene-vinyl alcohol copolymer, polyethylene terephthalate, polyvinylidene chloride, and ethylene-vinyl acetate copolymer. These materials may be combined by lamination.

Second Embodiment: Peritoneal Dialysate Set

A second embodiment of the present invention relates to a peritoneal dialysate set including a first peritoneal dialysate that contains 1.5 to 1.8 w/v % of glucose and 120 to 130 mEq/L of sodium; and a second peritoneal dialysate that contains 1.35 to 2.5 w/v % of glucose and 132 to 135 mEq/L of sodium, wherein the first peritoneal dialysate and the second peritoneal dialysate are independently used three to five times in total a day in peritoneal dialysis that involves injection of an amount of 1.5 to 2.0 L in an abdominal cavity of a subject, storage and drainage, in which the first peritoneal dialysate is used once or twice a day. With such constituent, it now becomes possible, in peritoneal dialysis treatment, to properly manage balance between water and sodium, without causing hyponatremia, and while avoiding any adverse effect exerted on the residual renal function.

Since the "first peritoneal dialysate", the "second peritoneal dialysate" and the "peritoneal dialysis" in the second embodiment are same as those in the first embodiment, so that explanations therefor will be skipped.

Third Embodiment: Composition Used for Peritoneal Dialysis

A third embodiment of the present invention relates to a composition for use in peritoneal dialysis, wherein the composition includes 1.5 to 1.8 w/v % of glucose and 120 to 130 mEq/L of sodium, wherein the composition is used in combination with another composition containing 1.35 to 2.5 w/v % of glucose and 132 to 135 mEq/L of sodium for use in peritoneal dialysis, wherein the composition and the another composition are independently injected in an amount of 1.5 to 2.0 L in an abdominal cavity of a subject, stored and drained three to five times in total a day, in which the composition is used once or twice a day. With such constituent, it now becomes possible, in peritoneal dialysis treatment, to properly manage balance between water and sodium, without causing hyponatremia, and while avoiding any adverse effect exerted on the residual renal function.

In the third embodiment, the "composition used for peritoneal dialysis" corresponds to the "first peritoneal dialysate" in the first embodiment, and the "another composition used for peritoneal dialysis" corresponds to the "second peritoneal dialysate" in the first embodiment, and the "peritoneal dialysis" is same as that in first embodiment, so that explanations therefor will be skipped.

Fourth Embodiment: Method for Peritoneal Dialysis

A fourth embodiment of the present invention relates to a method for peritoneal dialysis including: injecting independently each a first peritoneal dialysate and a second peritoneal dialysate in an amount of 1.5 to 2.0 L in an abdominal cavity of a subject, storing and draining three to five times in total a day, wherein the first peritoneal dialysate contains 1.5 to 1.8 w/v % of glucose and 120 to 130 mEq/L of sodium, and is used once or twice a day, and the second peritoneal dialysate contains 1.35 to 2.5 w/v % of glucose and 132 to 135 mEq/L of sodium. With such constituent, it now becomes possible, in peritoneal dialysis treatment, to properly manage balance between water and sodium, without causing hyponatremia, and while avoiding any adverse effect exerted on the residual renal function.

Since the "first peritoneal dialysate", the "second peritoneal dialysate" and the "peritoneal dialysis" in the fourth embodiment are same as those in the first embodiment, so that explanations therefor will be skipped.

EXAMPLES

Effects of the present invention will be explained, referring to Examples and Comparative Examples below. Note, however, that the technical scope of the present invention will not be limited by the Examples below. Note also that notations occasionally using "part(s)" or "%" in Examples below represent "part(s) by weight" or "% by weight", respectively, unless otherwise specifically noted. In addition, unless otherwise specifically noted, the individual operations are carried out at room temperature (1 to 30° C.)

<Preparation of Peritoneal Dialysate>

Necessary amounts of anhydrous glucose, sodium chloride, calcium chloride dihydrate, magnesium chloride hexahydrate and sodium. L-lactate solutions were measured so as to attain individual concentrations of glucose, sodium, calcium, magnesium, chlorine, and lactate ion as shown in Table 1, the peritoneal dialysates were prepared according to a method for preparing injections specified in General Rules for Preparations, The Japanese Pharmacopoeia, and then filtered through a membrane filter. The filtered dialysates were dispensed in polypropylene containers for peritoneal perfusion in compliance with the dual chamber container test, and tightly closed. The containers were tightly enclosed with packaging bags made of multi-layered laminate film, and sterilized with high pressure steam.

TABLE 1

|  | First peritoneal dialysate X | Peritoneal dialysate Y (Non-Patent Literature 3) | Second peritoneal dialysate A | Second peritoneal dialysate B |
|---|---|---|---|---|
| Glucose (w/v %) | 1.6 | 2.5 | 1.35 | 2.5 |
| $Na^+$ (mEq/L) | 126 | 118 | 135 | 135 |
| $Ca^{2+}$ (mEq/L) | 3.5 | 3.5 | 4 | 4 |
| $Mg^{2+}$ (mEq/L) | 0.5 | 0.5 | 1.5 | 1.5 |
| $Cl^-$ (mEq/L) | 95 | 87 | 105.5 | 105.5 |
| Lactate ion (mEq/L) | 35 | 35 | 35 | 35 |

Test Example 1

Clinical test below was conducted involving participants with chronic renal failure, having been undergoing peritoneal dialysis.

(Inclusion Criteria)

The test was targeted at the participants who met the criteria below, with consent ability.

(1) Participants having been undergoing peritoneal dialysis, from more than 6 months before the start of clinical trial.
(2) Participants having been undergoing peritoneal dialysis using peritoneal dialysate A or peritoneal dialysate B, from more than one month before the start of clinical trial.
(3) Age and gender: aged 20 and over (when the consent form was signed), any gender.
(4) Inpatient or outpatient: any.

(Exclusion Criteria)

(1) Participants having been using peritoneal dialysate with a glucose concentration of 4.0%.
(2) Participants with hypotension (with systolic blood pressure lower than 100 mmHg).
(3) Participants with low serum sodium concentration (less than 130 mEq/L) or with symptomatic hyponatremia.
(4) Participants having developed peritonitis within 2 months before the start of clinical trial.
(5) Participants not having passed 3 months after parathyroidectomy.
(6) Participants having serious complications in liver, heart, lungs, etc., or serious blood abnormalities.
(7) Participants having developed renal failure accompanied by serious disease such as cancer.
(8) Pregnant, lactating or possibly pregnant participants.
(9) Female participants who are fertile but incapable of having proper contraception during the clinical trial.
(10) Participants having participated other clinical trial within 6 months before the start of this clinical trial.
(11) Any other participants judged to be improper by the principal investigator or the subinvestigator of the clinical trial.

(Exit Criteria)

The clinical trial principal investigator (subinvestigator) withdrew the participant from the study, if any of the following conditions below applied.

(1) When withdrawal from the clinical trial was offered by a participant or a legal representative, etc.
(2) When the participant appeared to be not applicable, after the clinical trial has started.
(3) When the illness worsened to make the participant difficult to continue the clinical trial.
(4) An adverse event appeared to make the participant difficult to continue the clinical trial.
(5) In any other cases where the principal investigator or the subinvestigator deemed that withdrawal is necessary.

(Group Structure)

Thirty participants for peritoneal dialysis were grouped according to number of consumptions of the second peritoneal dialysate B, the breakdown being twelve participants in Group 1, six participants in Group 2, eight participants in Group 3, and four participants in Group 4.

Group 1: participants consuming no container of second peritoneal dialysate B.
Group 2: participants consuming one container of second peritoneal dialysate B.
Group 3: participants consuming two containers of second peritoneal dialysate B.
Group 4: participants consuming three or more containers of second peritoneal dialysate B.

(Administration Schedule)

The participants under sustained peritoneal dialysis treatment using the second peritoneal dialysate A or the second peritoneal dialysate B, being administered independently or in a combined manner, were evaluated over one day. After intervals of 2 to 5 weeks, the same participants were treated by peritoneal dialysis while leaving the formulations unchanged for the same participants, but replacing the second peritoneal dialysate A with the first peritoneal dialysate X, and replacing the second peritoneal dialysate B with the peritoneal dialysate Y, and then evaluated over one day. Table 2 summarizes the breakdown of the formulation and the number of cases, and Table 3 summarizes the total number of times of usage of the individual peritoneal dialysates.

TABLE 2

Breakdown of Formulation

| Group name | Breakdown of one day formulation | Breakdown of one day formulation | Number of cases |
|---|---|---|---|
| Group 1 | A, 3 times | → X, 3 times | 1 case |
|  | A, 4 times | → X, 4 times | 10 cases |
|  | A, 5 times | → X, 5 times | 1 case |
| Group 2 | B, once + A, twice | → Y, once + X, twice | 1 case |
|  | B, once + A, three times | → Y, once + X, three times | 5 cases |

TABLE 2-continued

Breakdown of Formulation

| Group name | Breakdown of one day formulation | Breakdown of one day formulation | Number of cases |
|---|---|---|---|
| Group 3 | B, twice + A, twice | → Y, twice + X, twice | 7 cases |
|  | B, twice + A, three times | → Y, twice + X, three times | 1 case |
| Group 4 | B, three times + A, once | → Y, three times + X, once | 3 cases |
|  | B, five times | → Y, five times | 1 case |

TABLE 3

Total Number of Times of Usage of Peritoneal Dialysates

| Group name | Peritoneal dialysate | Number of times | Peritoneal dialysate | Number of times |
|---|---|---|---|---|
| Group 1 | A | 48 times | X | 48 times |
| Group 2 | A | 17 times | X | 17 times |
|  | B | 6 times | Y | 6 times |
| Group 3 | A | 17 times | X | 17 times |
|  | B | 16 times | Y | 16 times |
| Group 4 | A | 3 times | X | 3 times |
|  | B | 14 times | Y | 14 times |

(Dosage and Administration)

The thus prepared peritoneal dialysate was injected in an amount of 1.5 to 2.0 L in the abdominal cavity, followed by storage for 4 to 8 hours and drainage after expecting the effects. These operations made up one cycle, and three to five times continuous operation per one day normally were continuously conducted using the second peritoneal dialysate A and the second peritoneal dialysate B which were properly combined or used independently. In regard to the first peritoneal dialysate X and the peritoneal dialysate Y, the same operation was continuously conducted, while replacing the second peritoneal dialysate A with the first peritoneal dialysate X, and replacing the second peritoneal dialysate B with the peritoneal dialysate Y.

Injection volume, storage time and number of times of operation were properly increased or decreased depending on symptom, blood biochemical values and imbalance of body fluid, age, body weight and so forth. Injection rate and drainage rate were usually controlled to 300 mL/min or below.

(Prohibited Concomitant Medication and Therapy)

During the evaluation period, usage of the second peritoneal dialysate A and the second peritoneal dialysate B was strictly required for all the time when the first peritoneal dialysate X and the peritoneal dialysate Y were not used, prohibiting the usage of any other peritoneal dialysate. Also any dialysis treatment other than peritoneal dialysis was prohibited.

<Evaluation>

Using the drainage and urine, collected and sampled from the participants, calculated were water removal (mL/cycle) and salt removal amount (g/cycle) per peritoneal dialysate, as well as water removal (mL/day), urinary volume (mL/day), amount of salt removal by peritoneal dialysis (g/day), urinary salt excretion (g/day), and recommended salt intake (g/day) specified in the Guidelines for Peritoneal Dialysis (2009 Edition, The Japanese Society of Dialysis Therapy (*J. Jpn. Soc. Dial. Ther.*, 42: 285-315, 2009)) per day, according to the methods below.

(Water Removal per Cycle of Peritoneal Dialysate (mL/Cycle))

Water removal(mL/cycle)=Drainage volume(mL/cycle)−Injection volume(mL/cycle).

(Amount of Salt Removal per Cycle of Peritoneal Dialysate (g/Cycle))

Amount of salt removal(g/cycle)=(Na concentration in drainage(mEq/L)×drainage volume(L/cycle)−Na concentration in dialysate(mEq/L)×injection volume (L/cycle))×0.0585.

(Daily Ultrafiltration Volume (mL/Day))

Water Removal(mL/day)=Daily total of water removal per peritoneal dialysate(mL/cycle).

(Daily Urinary Volume (mL/Day))

Urinary volume(mL/day)=Daily pooled urine(mL).

(Daily Amount of Salt Removal by Peritoneal Dialysis (g/Day))

Amount of salt removal(g/day)=Daily total of amount of salt removal per peritoneal dialysate (g/cycle).

(Daily Urinary Salt Excretion (g/Day))

Urinary salt excretion(g/Day)=Urinary sodium concentration(mEq/L)×urinary volume(L/day)×0.0585.

(Recommended Salt Intake (g/Day) Specified in the Guidelines for Peritoneal Dialysis)

Salt intake(g/day)=Water removal(L/day)×7.5 g+0.5 g per 100 mL of urinary volume.

<Results>

Figure 1:
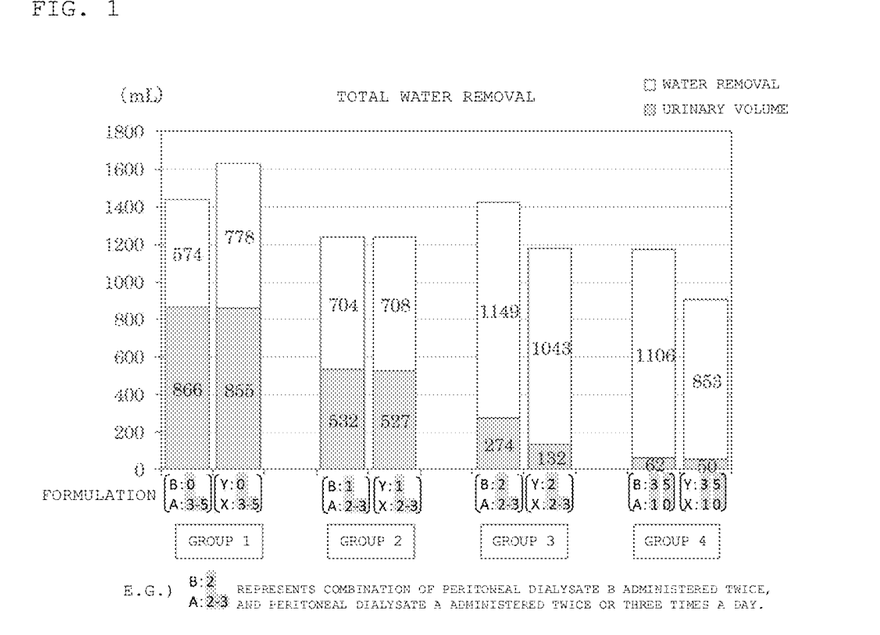
FIG. 1 illustrates total volume of daily water removal in Test Example 1.
Figure 2:
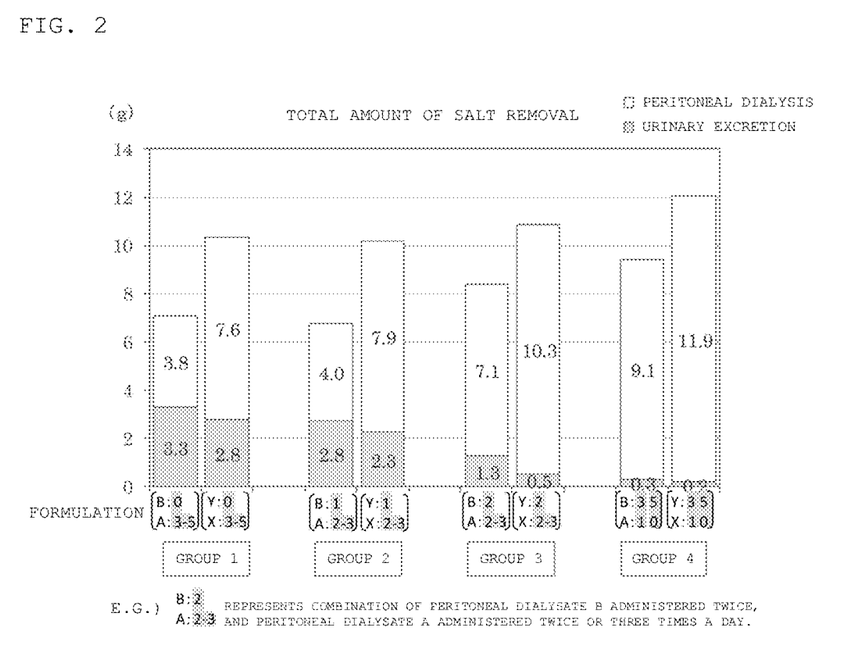
FIG. 2 illustrates total amount of daily salt removal in Test Example 1.
Figure 3:
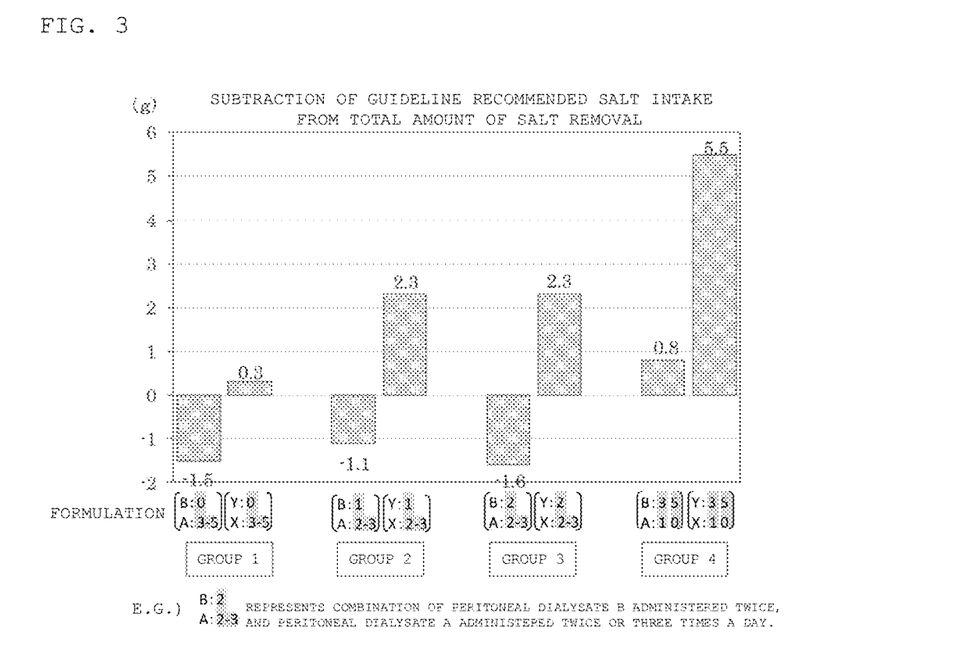
FIG. 3 illustrates values remained after subtracting the recommended salt intake according to the Guidelines for Peritoneal Dialysis, from the total amount of daily salt removal in Test Example 1.

Table 4 summarizes daily water removal (mL/day), daily urinary volume (mL/day), daily amount of salt removal (g/day) by peritoneal dialysis, daily urinary salt excretion (g/day), and recommended salt intake (g/day) specified in the Guidelines for Peritoneal Dialysis. Using average values of these items, the total volume of daily water removal and the total amount of daily salt removal were calculated. FIG. 1 illustrates the daily total water removal, and FIG. 2 illustrates the total amount of daily salt removal for each group. FIG. 3 illustrates values remained after subtracting the recommended salt intake specified in the Guidelines for Peritoneal Dialysis from the total amount of daily salt removal (sum of daily amount of salt removal by peritoneal dialysis and daily urinary salt excretion) for each group. Negative values mean that the salt removal is insufficient, whereas positive values mean that the salt removal is excessive. Table 5 summarizes water removal (mL/cycle) and salt removal amount (g/cycle) with the second peritoneal dialysate A, the second peritoneal dialysate B and the first peritoneal dialysate X, per cycle of peritoneal dialysis.

TABLE 4

| Peritoneal dialysate | Group 1 | Group 2 | Group 3 | Group 4 |
|---|---|---|---|---|
| Daily Water Removal (mL/day) | | | | |
| A, B | 574 ± 288 (12) | 704 ± 351 (6) | 1149 ± 445 (8) | 1106 ± 334 (4) |
| X, Y | 778 ± 242 (12) | 708 ± 521 (6) | 1043 ± 507 (8) | 853 ± 431 (4) |

TABLE 4-continued

| Peritoneal dialysate | Group 1 | Group 2 | Group 3 | Group 4 |
|---|---|---|---|---|
| Daily Urinary Volume (mL/day) | | | | |
| A, B | 866 ± 575 (12) | 532 ± 579 (6) | 274 ± 510 (8) | 62 ± 72 (4) |
| X, Y | 855 ± 618 (12) | 527 ± 552 (6) | 132 ± 200 (8) | 50 ± 58 (4) |
| Daily Amount of Salt Removal by Peritoneal Dialysis (g/day) | | | | |
| A, B | 3.8 ± 1.3 (12) | 4.0 ± 1.6 (6) | 7.1 ± 2.6 (8) | 9.1 ± 1.5 (4) |
| X, Y | 7.6 ± 2.0 (12) | 7.9 ± 3.6 (6) | 10.3 ± 3.8 (8) | 11.9 ± 2.1 (4) |
| Daily Urinary Salt Excretion (g/day) | | | | |
| A, B | 3.3 ± 2.5 (12) | 2.8 ± 3.4 (6) | 1.3 ± 2.5 (8) | 0.3 ± 0.4 (4) |
| X, Y | 2.8 ± 2.4 (12) | 2.3 ± 2.7 (6) | 0.5 ± 0.8 (8) | 0.2 ± 0.3 (4) |
| Recommended Salt Intake (g/day) Specified in the Guidelines for Peritoneal Dialysis | | | | |
| A, B | 8.6 ± 3.3 (12) | 7.9 ± 1.9 (6) | 10.0 ± 3.2 (8) | 8.6 ± 2.4 (4) |
| X, Y | 10.1 ± 2.7 (12) | 7.9 ± 2.4 (6) | 8.5 ± 3.6 (8) | 6.6 ± 3.1 (4) |

Average ± standard deviation (n)

TABLE 5

| Peritoneal dialysate | Group 1 | Group 2 | Group 3 |
|---|---|---|---|
| Water removal (mL/cycle) of Individual Peritoneal Dialysates | | | |
| A | 143 ± 146 (48) | 104 ± 125 (17) | 135 ± 166 (17) |
| B | | 408 ± 187 (6) | 431 ± 172 (16) |
| X | 194 ± 84 (48) | 138 ± 205 (17) | 184 ± 144 (17) |
| Amount of Salt Removal (g/cycle) of Individual Peritoneal Dialysates | | | |
| A | 0.9 ± 1.0 (48) | 0.6 ± 0.8 (17) | 0.9 ± 1.3 (17) |
| B | | 2.4 ± 1.3 (6) | 2.6 ± 1.0 (16) |
| X | 1.9 ± 0.7 (48) | 1.6 ± 1.6 (17) | 1.91 ± 1.2 (17) |

Average ± standard deviation (n)

DISCUSSION

Interrelations among the residual renal function (urinary volume), the peritoneal dialysis, and the amount of salt removal were clarified first by the present tests. Details will be described below.

1) Depressed condition of the residual renal function is understood to be predictable from the number of consumptions of the second peritoneal dialysate B. Increased number of consumptions of the peritoneal dialysate with high glucose concentration would be more likely to make the water removal excessive as known from FIG. 1, possibly degrading water balance to worsen the residual renal function.

2) Use of the low sodium peritoneal dialysate (s) (first peritoneal dialysate X, or combination of first peritoneal dialysate X and peritoneal dialysate Y) alone is understood to pose a risk of hyponatremia. As can be seen in FIG. 3, the cases using the low sodium peritoneal dialysates, particularly Groups 2 to 4 using the peritoneal dialysate Y, were found to excessively remove salt. Considering that these results were given by the administration only for one day, everyday administration solely based on combination of the first peritoneal dialysate X and the peritoneal dialysate Y would pose a risk of hyponatremia.

3) As can be understood from FIGS. 1 and 2, even when the amount of salt removal was enhanced by using the low sodium peritoneal dialysate(s) (first peritoneal dialysate X, or combination of first peritoneal dialysate X and peritoneal dialysate Y), as compared with the amount of salt removal attainable by the existing peritoneal dialysate(s) (second peritoneal dialysate A, or combination of second peritoneal dialysate A and second peritoneal dialysate B), Groups 1 and 2 with sufficient urinary volume (500 mL or more) showed only insignificant changes of urinary volume (FIG. 1), while the urinary salt excretion showed declining tendencies (FIG. 2).

4) As can be understood from FIGS. 1 and 2, enhanced salt removal by peritoneal dialysis would adversely affect the residual renal function in Group 3 with oliguria (defined by a daily urinary volume of 400 mL or less). This was, however, found to be no longer influential in Group 4 with anuria (defined by a daily urinary volume of 100 mL or less).

5) Judging from data of Group 1 in FIGS. 1 and 3, the first peritoneal dialysate X alone might be supposedly suitable to keep good water balance and sodium balance. An adverse event (abnormal change of blood sodium concentration: normal value to abnormal value) was, however, found in one case using the first peritoneal dialysate X five times a day. This suggests that the number of times of usage of peritoneal dialysate X has to be limited.

6) As can be understood from FIG. 3, for good balancing with salt intake recommended by the Guidelines for Peritoneal Dialysis, Groups 1, 2 and 3 may only enhance approximately 1 to 2 g of the daily amount of salt removal by peritoneal dialysis, from the amount of salt removal attainable by the existing peritoneal dialysate(s) (second peritoneal dialysate A, or combination of second peritoneal dialysate A and peritoneal dialysate B).

7) As can be understood from Table 5, the first peritoneal dialysate X showed the amount of salt removal per cycle of peritoneal dialysis, which was approximately 1 g larger in all of Groups 1, 2 and 3, as compared with the second peritoneal dialysate A.

Judging from 1) to 7) above, the peritoneal dialysates disclosed in Patent Literature 4 and Non-Patent Literature 3, although capable of suppressing the sodium residence to almost zero, would however pose a risk of hyponatremia due to excessive salt removal, when clinically used independently or in a combined manner, and would further pose a problem of adverse effect possibly exerted on the residual renal function.

Test Example 2

Figure 4:
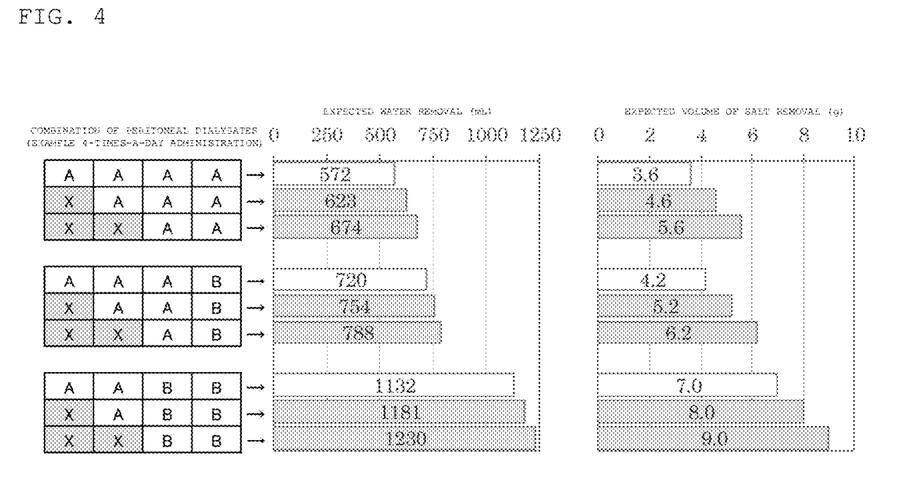
FIG. 4 illustrates daily expected water removal and expected amount of salt removal in Test Example 2.

To address the aforementioned problem, further investigations were made using data obtained in Test Example 1, to thereby calculate daily expected water removal (mL/day) and daily expected amount of salt removal (g/day), for the case where combinations of the first peritoneal dialysate X with the second peritoneal dialysate A and/or the second peritoneal dialysate B were employed. Results are illustrated in FIG. 4. As can be understood from FIG. 4, use of the number of daily consumption of the first peritoneal dialysate X limited to one or two, with the residue to be combined being assigned to the second peritoneal dialysate A and/or the second peritoneal dialysate B, can widen treatment options regarding ultrafiltration and salt removal than before, and can properly manage the balance between water and sodium while avoiding adversely affecting the residual renal function.

Figure 5:
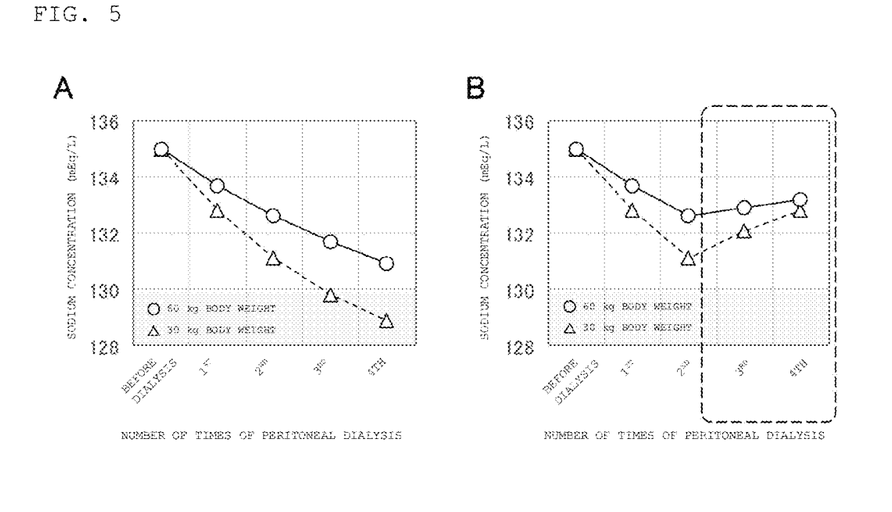
FIG. 5 illustrates results of simulation for finding degree of dilution of sodium concentration in extracellular fluid, when injected peritoneal dialysate were completely absorbed by living bodies.

In this mode of usage, a risk of hyponatremia is avoidable as can be understood from FIG. 5, even if drainage trouble should occur twice in a row during use of the first peritoneal dialysate X.

FIG. 5 illustrates results of simulation for finding degree of dilution of sodium concentration in extracellular fluid, when injected peritoneal dialysate were completely absorbed by living bodies.

Calculations are conducted specifically as follows. Considering that the volume of extracellular fluid accounts for 20% of body weight on the basis of water distribution of body fluid, a 60-kg participant will have a volume of extracellular fluid of 12 L. Assuming now that 2 L of the first peritoneal dialysate X (Na concentration=126 mEq/L) were completely absorbed in the living body due to drainage trouble, the extracellular fluid with a Na concentration of 135 mEq/L is diluted down to 133.7 mEq/L, as calculated using the equation below.

$$(135 \times 12 + 126 \times 2)/(12+2) = 133.7 \quad [\text{Math. 1}]$$

Similarly, in the second cycle, the extracellular fluid having a Na concentration of 133.7 mEq/L is diluted down to 132.6 mEq/L, as calculated using the equation below.

$$(133.7 \times 12 + 126 \times 2)/(12+2) = 132.6 \quad [\text{Math. 2}]$$

The calculation is repeated four times to yield a result for a 60-kg participant. Similar calculation is also made on a 30-kg participant.

For more strict conditions, the body weights are fixed, and the volume of extracellular fluid is calculated at a percentage of 20% of body weight. Results are illustrated in FIG. 5A.

In the subsequent 3rd and 4th cycles, the Na concentration of the extracellular fluid is corrected to 135 mEq/L, by replacing the peritoneal dialysate with the existing peritoneal dialysate having a standard Na concentration (135 mEq/L). Results are illustrated in FIG. 5B.

While lighter participants are naturally considered to be more strongly affected, a 30-kg participant is however not considered to have a sodium concentration of the extracellular fluid fallen below 130 mEq/L, if the drainage trouble occurred twice or less. It has widely been known that no clinical symptom will appear usually down to a level of 130 mEq/L.

Accordingly, as can be understood from FIGS. 4 and 5, in peritoneal dialysis treatment, it now becomes possible to properly manage the balance between water and sodium, without causing hyponatremia, while avoiding adversely affecting the residual renal function, by limiting the number of daily consumption of the first peritoneal dialysate X to one or two, with the residue to be combined being assigned to the second peritoneal dialysate A and/or the second peritoneal dialysate B.

The present invention is based on Japanese Patent Application No. 2018-036394 filed on Mar. 1, 2018, the entire contents of which are incorporated herein by reference into the present disclosure.

The invention claimed is:

1. A peritoneal dialysate set for performing peritoneal dialysis on a single subject in a single day, the peritoneal dialysate set comprising:
   a first volume of a first peritoneal dialysate solution that contains 1.5 to 1.8 w/v % of glucose and 120 to 130 mEq/L of sodium; and
   a second volume of a second peritoneal dialysate solution that contains 1.35 to 2.5 w/v % of glucose and 132 to 135 mEq/L of sodium,
   the first volume of the first peritoneal dialysate solution and the second volume of the second peritoneal dialysate solution totaling at least 4.5 L;
   the peritoneal dialysate set being constituted so that the first peritoneal dialysate solution and the second peritoneal dialysate solution are independently injected during the peritoneal dialysis and so that the total volume of at least 4.5 L is injected in an abdominal cavity of the single subject in the single day.

2. The peritoneal dialysate set according to claim 1, wherein the first peritoneal dialysate solution comprises 123 to 128 mEq/L of sodium.

3. The peritoneal dialysate set according to claim 1, wherein the first peritoneal dialysate solution comprises 2.0 to 4.0 m Eq/L of calcium; 0.5 to 1.5 mEq/L of magnesium; 86.0 to 98.0 m Eq/L of chlorine; and 35 to 40 mEq/L of an alkalizing agent.

4. The peritoneal dialysate set according to claim 1, wherein the second peritoneal dialysate solution comprises 2.3 to 4.0 m Eq/L of calcium; 0.5 to 1.5 m Eq/L of magnesium; 95.0 to 105.5 m Eq/L of chlorine; and 35 to 40 m Eq/L of an alkalizing agent.

5. A combination for performing peritoneal dialysis on a single subject in a single day, the combination comprising:
   a first composition containing 1.5 to 1.8 w/v % of glucose and 120 to 130 mEq/L of sodium; and
   a second composition containing 1.35 to 2.5 w/v % of glucose and 132 to 135 m Eq/L of sodium,
   combination including a total volume of the first and second composition that (i) allows the first composition to be independently injected in an amount of 1.5 to 2.0 L, once or twice a day, in an abdominal cavity of the single subject in the single day, and (ii) allows the second composition to be independently injected in an amount of 1.5 to 2.0 L, at least twice a day, in the abdominal cavity of the single subject in the single day.

6. A method for performing peritoneal dialysis in a single subject in a single day comprising:
   administering a first peritoneal dialysate solution to the single subject at least once in the single day, the administering of the first peritoneal dialysate solution including:
   injecting 1.5 L to 2.0 L of the first peritoneal dialysate solution into an abdominal cavity of the single subject, storing the first peritoneal dialysate solution in the abdominal cavity and draining the first peritoneal dialysate solution from the abdominal cavity; and
   administering a second peritoneal dialysate solution to the single subject at least twice in the single day, the administering of the second peritoneal dialysate solution including:
   injecting 1.5 L to 2.0 L of the second peritoneal dialysate solution into the abdominal cavity of the single subject, storing the second peritoneal dialysate solution in the abdominal cavity and draining the second peritoneal dialysate solution from the abdominal cavity, the injecting of the first peritoneal dialysate solution and the injecting of the second peritoneal dialysate solution being independent of one another, wherein the first peritoneal dialysate solution contains 1.5 to 1.8 w/v % of glucose and 120 to 130 m Eq/L of sodium, and the second peritoneal dialysate solution contains 1.35 to 2.5 w/v % of glucose and 132 to 135 m Eq/L of sodium.

7. The method according to claim 6, wherein the administering of the first peritoneal dialysate solution to the single subject occurs once or twice in the single day, and the administering of the second peritoneal dialysate solution occurs three to five times in the single day.

8. A peritoneal dialysate set for performing peritoneal dialysis on a single subject in a single day, the peritoneal dialysate set comprising:

at least one container holding 1.5 L to 2.0 L of a first peritoneal dialysate solution that contains 1.5 to 1.8 w/v % of glucose and 120 to 130 mEq/L of sodium;

at least two containers each holding 1.5 L to 2.0 L of a second peritoneal dialysate solution that contains 1.35 to 2.5 w/v % of glucose and 132 to 135 m Eq/L of sodium; and the peritoneal dialysate set being constituted so that the first peritoneal dialysate solution and the second peritoneal dialysate solution are independently injected during the peritoneal dialysis and so that the total volume of at least 4.5 L is injected in an abdominal cavity of the single subject in the single day.

\* \* \* \* \*